(12) United States Patent
Guo et al.

(10) Patent No.: US 10,532,077 B2
(45) Date of Patent: Jan. 14, 2020

(54) VIRUS-LIKE PARTICLE OF SENECAVIRUS A

(71) Applicant: Lanzhou Veterinary Research Institute Chinese Academy of Agricultural Sciences, Lanzhou (CN)

(72) Inventors: Huichen Guo, Lanzhou (CN); Shiqi Sun, Lanzhou (CN); Shichong Han, Lanzhou (CN); Hu Dong, Lanzhou (CN); Xiaoran Guo, Lanzhou (CN); Hong Yin, Lanzhou (CN); Jianxun Luo, Lanzhou (CN)

(73) Assignee: LANZHOU VETERINARY RESEARCH INSTITUTE CHINESE ACADEMY OF AGRICULTURAL SCIENCES, Lanzhou (CN)

( * ) Notice: Subject to any disclaimer, the term of this patent is extended or adjusted under 35 U.S.C. 154(b) by 0 days.

(21) Appl. No.: 16/413,598

(22) Filed: May 15, 2019

(65) Prior Publication Data

US 2019/0350990 A1 Nov. 21, 2019

(30) Foreign Application Priority Data

May 18, 2018 (CN) .......................... 2018 1 0483236

(51) Int. Cl.
| | | |
|---|---|---|
| *C07K 14/005* | (2006.01) | |
| *C07K 16/10* | (2006.01) | |
| *C12N 7/00* | (2006.01) | |
| *A61K 39/00* | (2006.01) | |
| *A61K 39/12* | (2006.01) | |
| *A61K 35/76* | (2015.01) | |
| *C12N 15/86* | (2006.01) | |
| *A61P 31/14* | (2006.01) | |
| *A61K 39/39* | (2006.01) | |

(52) U.S. Cl.
CPC .............. *A61K 35/76* (2013.01); *A61K 39/12* (2013.01); *A61K 39/39* (2013.01); *A61P 31/14* (2018.01); *C07K 16/1009* (2013.01); *C12N 15/86* (2013.01); *C12N 2770/32034* (2013.01)

(58) Field of Classification Search
CPC .... C07K 14/005; C07K 16/1009; C12N 7/00; A61K 2039/523; A61K 2039/5254
See application file for complete search history.

*Primary Examiner* — Barry A Chestnut
(74) *Attorney, Agent, or Firm* — Matthias Scholl P.C.; Matthias Scholl

(57) ABSTRACT

A virus-like particle of Senecavirus A, the particle including a structural protein VP0, a structural protein VP1 and a structural protein VP3. The structural protein VP0 is encoded by a gene sequence represented by SEQ ID NO: 1. The structural protein VP1 is encoded by a gene sequence represented by SEQ ID NO: 2. The structural protein VP3 is encoded by a gene sequence represented by SEQ ID NO: 3.

6 Claims, 2 Drawing Sheets

Specification includes a Sequence Listing.

SEQUENCE LISTING

```
<160> NUMBER OF SEQ ID NOS: 22

<210> SEQ ID NO 1
<211> LENGTH: 1065
<212> TYPE: DNA
<213> ORGANISM: Artificial Sequence
<220> FEATURE:
<223> OTHER INFORMATION: Fully synthetic

<400> SEQUENCE: 1
ggcaacgttc aaaccaccag caagaacgac ttcgatagcc gtggcaacaa cggtaacatg     60
acctttaact actatgcgaa cacctaccag aacagcgtgg acttcagcac cagcagcagc    120
```

```
gcgagcggtg cgggtccggg taacagccgt ggtggcctgg cgggtctgct gaccaacttt    180
agcggcatcc tgaacccgct gggttatctg aaggaccaca acaccgagga aatggagaac    240
agcgcggatc gtgttatcac ccaaaccgcg ggcaacaccg cgattaacac ccagagcagc    300
ctgggtgttc tgtgcgcgta cgtggaagac ccgaccaaaa gcgatccgcc gagcagcagc    360
accgaccagc cgaccaccac cttcaccgcg attgatcgtt ggtataccgg ccgtctgaac    420
agctggacca aggcggttaa aaccttcagc tttcaagcgg tgccgctgcc gggtgcgttt    480
ctgagccgtc agggtggcct gaacggtggc gcgttcaccg cgaccctgca ccgtcacttt    540
ctgatgaagt gcggctggca ggtgcaagtt cagtgcaacc tgacccaatt ccaccagggt    600
gcgctgctgg ttgcgatggt gccggagacc accctggacg ttaagccgga tggcaaggcg    660
aaaagcctgc aagagctgaa cgaggaacag tgggtggaaa tgagcgacga ttaccgtacc    720
ggcaaaaaca tgccgtttca agcctgggt  acctactatc gtccgccgaa ctggacctgg    780
ggtccgaact tcatcaaccc gtaccaagtg accgttttc  cgcaccagat tctgaacgcg    840
cgtaccagca ccagcgttga catcagcgtg ccgtatattg cgagaccccc gacccaaagc    900
agcgaaaccc agaacagctg gaccctgctg gtgatggttc tggtgccgct ggactacaaa    960
gagggtgcga ccaccgatcc ggaaatcacc ttcagcgtgc gtccgaccag cccgtatttc   1020
aacggcctgc gtaaccgttt taccaccggt accgatgagg aacag                   1065

<210> SEQ ID NO 2
<211> LENGTH: 792
<212> TYPE: DNA
<213> ORGANISM: Artificial Sequence
<220> FEATURE:
<223> OTHER INFORMATION: Fully synthetic

<400> SEQUENCE: 2
agcaccgaca acgcggagac cggtgtgatc gaagcgggca acaccgacac cgatttcagc     60
ggcgagctgg cggcgccggg cagcaaccac accaacgtga agttcctgtt tgaccgtagc    120
cgtctgctga acgttattaa ggtgctggaa aaagatgcgg ttttccgcg  tccgtttccg    180 accgcgaccg gtacccagca agacgatggc tatttctgcc tgctgacccc cgtccgacc    240 gttgcgagcc gtccggcgac ccgttttggt ctgtacgtga cccgagcga cagcggcgtt    300 ctggcgaaca ccagcctgga tttcaacttt tacagcctgg cgtgcttcac ctatttcgt    360 agcgacctgg aagtgaccgt ggttagcctg gagccggatc tggaattcgc ggttggttgg    420
tttccgagcg gcagcgaata ccaggcgagc agcttcgtgt atgaccaact gcacgttccg    480
taccacttca gcggtcgtac cccgcgtgcg tttaccagca agggtggcaa agttagctt    540 gtgctgccgt ggaacagcgt tagcagcgtg ctgccggttc gttggggtgg cgcgagcaaa    600
ctgagcagcg cgacccgtgg tctgccggcg catgcggatt ggggtaccat ctatgcgttc    660
attccgcgtc cgaacgagaa gaaaagcacc gcggtgaagc acgtggcggt ttacgtgcgt    720
tataaaaacg cgcgtgcgtg gtgcccgagc atgctgccgt tcgtagcta  caagcagaaa    780 atgctgatgc aa                                                        792

<210> SEQ ID NO 3
<211> LENGTH: 717
<212> TYPE: DNA
<213> ORGANISM: Artificial Sequence
<220> FEATURE:
<223> OTHER INFORMATION: Fully synthetic

<400> SEQUENCE: 3
```

```
ggtccgattc cgaccgcgcc gcgtgagaac agcctgatgt tcctgagcac cattccggac      60
gataccgttc cggcgtacgg taacgtgcgt accccgccgg ttaactatct gccgggcgaa     120
atcaccgacc tgctgcaact ggcgcgtatt ccgaccctga tggcgtttgg tcgtgttagc     180
gagccggaac cggcgagcga tgcgtacgtt ccgtatgtgg cggttccggc gcagttcgac     240
gataagccgc tgatcagctt tccgattacc ctgagcgacc cggtgtacca aaacaccctg     300
gttggtgcga tcagcagcaa cttcgcgaac tatcgtggct gcatccagat acccctgacc     360
ttctgcggtc cgatgatggc gcgtggcaaa tttctgctga gctatagccc gccgaacggt     420
gcgcagccgc aaaccctgag cgaggcgatg caatgcacct atagcatctg gacattggc      480 ctgaacagca gctggacctt cgtgatcccg tacattagcc cgagcgacta tcgtgaaacc     540
cgtgcgatta ccaacagcgt ttacagcgcg gatggttggt ttagcctgca caagctgacc     600
aaaattaccc tgccgccgga ttgcccgcag agcccgtgca ttctgttctt tgcgagcgcg     660
ggtgaagact acaccctgcg tctgccggtg gattgcaacc cgagctatgt ttttcac       717
```

```
<210> SEQ ID NO 4
<211> LENGTH: 51
<212> TYPE: DNA
<213> ORGANISM: Artificial Sequence
<220> FEATURE:
<223> OTHER INFORMATION: Fully synthetic

<400> SEQUENCE: 4
gccatgggtc atcaccatca tcatcacggg tcggactcag aagtcaatca a              51

<210> SEQ ID NO 5
<211> LENGTH: 44
<212> TYPE: DNA
<213> ORGANISM: Artificial Sequence
<220> FEATURE:
<223> OTHER INFORMATION: Fully synthetic

<400> SEQUENCE: 5
ggatccgaga ccttaaggtc tcaacctcca atctgttcgc ggtg                      44

<210> SEQ ID NO 6
<211> LENGTH: 344
<212> TYPE: DNA
<213> ORGANISM: Artificial Sequence
<220> FEATURE:
<223> OTHER INFORMATION: Fully synthetic

<400> SEQUENCE: 6
gccatgggtc atcaccatca tcatcacggg tcggactcag aagtcaatca agaagctaag      60
ccagaggtca agccagaagt caagcctgag actcacatca atttaaaggt gtccgatgga     120
tcttcagaga tcttcttcaa gatcaaaaag accactcctt aagaaggct gatggaagcg      180 ttcgctaaaa gacagggtaa ggaaatggac tccttaagat tcttgtacga cggtattaga     240
attcaagctg atcaggcccc tgaagatttg gacatggagg ataacgatat tattgaggct     300
caccgcgaac agattggagg ttgagacctt aaggtctcag atcc                      344

<210> SEQ ID NO 7
<211> LENGTH: 27
<212> TYPE: DNA
<213> ORGANISM: Artificial Sequence
<220> FEATURE:
<223> OTHER INFORMATION: Fully synthetic
```

```
<400> SEQUENCE: 7
ggcggtacca ataaccctga taaatgc                                          27

<210> SEQ ID NO 8
<211> LENGTH: 28
<212> TYPE: DNA
<213> ORGANISM: Artificial Sequence
<220> FEATURE:
<223> OTHER INFORMATION: Fully synthetic

<400> SEQUENCE: 8
ccgcgctagc atgagattat caaaaagg                                         28

<210> SEQ ID NO 9
<211> LENGTH: 27
<212> TYPE: DNA
<213> ORGANISM: Artificial Sequence
<220> FEATURE:
<223> OTHER INFORMATION: Fully synthetic

<400> SEQUENCE: 9
gtcggtaccg aattaattca tgagcgg                                          27

<210> SEQ ID NO 10
<211> LENGTH: 27
<212> TYPE: DNA
<213> ORGANISM: Artificial Sequence
<220> FEATURE:
<223> OTHER INFORMATION: Fully synthetic

<400> SEQUENCE: 10
tcagctagcg accaaaatcc cttaacg                                          27

<210> SEQ ID NO 11
<211> LENGTH: 29
<212> TYPE: DNA
<213> ORGANISM: Artificial Sequence
<220> FEATURE:
<223> OTHER INFORMATION: Fully synthetic

<400> SEQUENCE: 11
aatggtacca aaaaattacg ccccgccct                                        29

<210> SEQ ID NO 12
<211> LENGTH: 27
<212> TYPE: DNA
<213> ORGANISM: Artificial Sequence
<220> FEATURE:
<223> OTHER INFORMATION: Fully synthetic

<400> SEQUENCE: 12
ctggacgcta gccaccatca tacacta                                          27

<210> SEQ ID NO 13
<211> LENGTH: 29
<212> TYPE: DNA
<213> ORGANISM: Artificial Sequence
<220> FEATURE:
<223> OTHER INFORMATION: Fully synthetic

<400> SEQUENCE: 13
ggtctctagg tggcaacgtt caaaccacc                                        29

<210> SEQ ID NO 14
<211> LENGTH: 30
```

<210> SEQ ID NO 14
<211> LENGTH: 30 (implied)
<212> TYPE: DNA
<213> ORGANISM: Artificial Sequence
<220> FEATURE:
<223> OTHER INFORMATION: Fully synthetic

<400> SEQUENCE: 14
cgcggatcct cactgttcct catcggtacc                                    30

<210> SEQ ID NO 15
<211> LENGTH: 29
<212> TYPE: DNA
<213> ORGANISM: Artificial Sequence
<220> FEATURE:
<223> OTHER INFORMATION: Fully synthetic

<400> SEQUENCE: 15
ggtctctagg tagcaccgac aacgcggag                                     29

<210> SEQ ID NO 16
<211> LENGTH: 30
<212> TYPE: DNA
<213> ORGANISM: Artificial Sequence
<220> FEATURE:
<223> OTHER INFORMATION: Fully synthetic

<400> SEQUENCE: 16
cgcggatcct cattgcatca gcattttctg                                    30

<210> SEQ ID NO 17
<211> LENGTH: 29
<212> TYPE: DNA
<213> ORGANISM: Artificial Sequence
<220> FEATURE:
<223> OTHER INFORMATION: Fully synthetic

<400> SEQUENCE: 17
ggtctctagg tggtccgatt ccgaccgcg                                     29

<210> SEQ ID NO 18
<211> LENGTH: 30
<212> TYPE: DNA
<213> ORGANISM: Artificial Sequence
<220> FEATURE:
<223> OTHER INFORMATION: Fully synthetic

<400> SEQUENCE: 18
cgcggatcct cagtgaaaaa catagctcgg                                    30

<210> SEQ ID NO 19
<211> LENGTH: 36
<212> TYPE: DNA
<213> ORGANISM: Artificial Sequence
<220> FEATURE:
<223> OTHER INFORMATION: Fully synthetic

<400> SEQUENCE: 19
ggcaatggat ccatgggtca tcaccatcat catcac                             36

<210> SEQ ID NO 20
<211> LENGTH: 35
<212> TYPE: DNA
<213> ORGANISM: Artificial Sequence
<220> FEATURE:
<223> OTHER INFORMATION: Fully synthetic

<400> SEQUENCE: 20

```
ggtaatctcg agttactgtt cctcatcggt accgg                              35

<210> SEQ ID NO 21
<211> LENGTH: 34
<212> TYPE: DNA
<213> ORGANISM: Artificial Sequence
<220> FEATURE:
<223> OTHER INFORMATION: Fully synthetic

<400> SEQUENCE: 21
ggccgtctcg agttattgca tcagcatttt ctgc                               34

<210> SEQ ID NO 22
<211> LENGTH: 34
<212> TYPE: DNA
<213> ORGANISM: Artificial Sequence
<220> FEATURE:
<223> OTHER INFORMATION: Fully synthetic

<400> SEQUENCE: 22
ggccttctcg agttagtgaa aaacatagct cggg                               34
```

VIRUS-LIKE PARTICLE OF SENECAVIRUS A

CROSS-REFERENCE TO RELATED APPLICATIONS

Pursuant to 35 U.S.C. § 119 and the Paris Convention Treaty, this application claims foreign priority to Chinese Patent Application No. 201810483236.3 filed May 18, 2018, the contents of which, including any intervening amendments thereto, are incorporated herein by reference. Inquiries from the public to applicants or assignees concerning this document or the related applications should be directed to: Matthias Scholl P.C., Attn.: Dr. Matthias Scholl Esq., 245 First Street, 18th Floor, Cambridge, Mass. 02142.

BACKGROUND

The disclosure relates to a virus-like particle of the Senecavirus A (SVA), a method of preparing the same, and use thereof.

Senecavirus is a genus of viruses in the order Picornavirales, in the family Picornaviridae. Pig and maybe also cow serve as natural hosts. There is currently only one species in this genus: the type species Senecavirus A.

When infected with Senecavirus A, pigs develop erosions, ulcerations, and vesicular lesions of the snout, oral mucosa, and distal limbs, especially around the coronary band. Hoof sloughing and lameness can also occur, as well as more general symptoms of illness such as fever, lethargy, and anorexia.

Virus-like particles (VLPs) resemble viruses but are non-infectious because they contain no viral genetic material. VLPs are widely used in the development of human and veterinary vaccines.

SUMMARY

The disclosure provides a virus-like particle of Senecavirus A and a method for preparing the same.

Disclosed is a virus-like particle of Senecavirus A, the particle comprising a structural protein VP0, a structural protein VP1 and a structural protein VP3. The structural protein VP0 is encoded by a gene sequence represented by SEQ ID NO: 1; the structural protein VP1 is encoded by a gene sequence represented by SEQ ID NO: 2; and the structural protein VP3 is encoded by a gene sequence represented by SEQ ID NO: 3.

The disclosure also provides a method for preparing a virus-like particle of the Senecavirus A, the method comprising:
(1) constructing a recombinant plasmid containing a gene sequence encoding the structural protein VP0, the structural protein VP1, or the structural protein VP3 of the Senecavirus A, where the gene sequence encoding the structural protein VP0 is represented by SEQ ID NO: 1, the gene sequence encoding the structural protein VP1 is represented by SEQ ID NO: 2, and the gene sequence encoding the structural protein VP3 is represented by SEQ ID NO: 3;
(2) expressing and purifying the structural protein VP0, the structural protein VP1 and the structural protein VP3 of the Senecavirus A; and
(3) assembling the virus-like particle of the Senecavirus A.

The method of preparing the virus-like particle of the Senecavirus A can comprise:
1) amplifying a smt3 gene using genomic DNA of *Saccharomyces cerevisiae* as a template and smt3F and smt3R as primers, the smt3F having a sequence of SEQ ID NO: 4, the smt3R having a sequence of SEQ ID NO: 5, and the smt3 gene having a sequence of SEQ ID NO: 6;
2) digesting the smt3 gene and a vector pET-28a using restriction enzymes Nco I and BamH I, inserting the digested smt3 gene into the digested pET-28a vector, to yield a vector pSMK; amplifying an AmpR gene using a pUC19 plasmid as a template and AmpRKpnI and AmpRNheI as primers, amplifying a DNA fragment from the pSMK using PSMKKpnI and PSMKNheI as primers, digesting the DNA fragment and the AmpR gene with restriction enzymes KpnI and NheI, and inserting the digested AmpR gene into the digested DNA fragment, to yield a vector pSMA; amplifying a CmR gene using the pACYC plasmid as a template and CmRKpnI and CmRNheI as primers, amplifying a DNA fragment from the pSMK using PSMKKpnI and PSMKNheI as primers, digesting the DNA fragment and the CmR gene with restriction enzymes KpnI and NheI, and inserting the digested CmR gene into the digested DNA fragment, to yield a vector pSMC; wherein the AmpRKpnI has a sequence of SEQ ID NO: 7, the AmpRNheI has a sequence of SEQ ID NO: 8, the PSMKKpnI has a sequence of SEQ ID NO: 9, the PSMKNheI has a sequence of SEQ ID NO: 10, the CmRKpnI has a sequence of SEQ ID NO: 11, and the CmRNheI has a sequence of SEQ ID NO: 12;
3) synthesizing coding genes of the structural proteins VP0, VP1 and VP3; amplifying the coding genes of the structural proteins VP0, VP1, and VP3 using the synthesized coding genes of the structural proteins VP0, VP1, and VP3 as templates and VP0F/VP0R, VP1F/VP1R, and VP3F/VP3R as primers, respectively; wherein a coding gene of the structural protein VP0 is represented by SEQ ID NO: 1, a coding gene of the structural protein VP1 is represented by SEQ ID NO: 2, and a coding gene of the structural protein VP3 is represented by SEQ ID NO: 3; the VP0F has a sequence of SEQ ID NO: 13, the VP0R has a sequence of SEQ ID NO: 14, the VP1F has a sequence of SEQ ID NO: 15, the VP1R has a sequence of SEQ ID NO: 16, the VP3F has a sequence of SEQ ID NO: 17, the VP3R has a sequence of SEQ ID NO: 18;
4) digesting the amplified coding genes of the structural proteins VP0, VP1, and VP3 using the restriction enzymes BsmBI/BamH I, digesting the vector pSMK, pSMA or pSMC using the restriction enzyme BsaI, inserting the digested coding genes of the structural proteins VP0, VP1, and VP3 into the digested pSMK, pSMA or pSMC, to yield recombinant expression vectors pSMK/VP0, pSMA/VP1, and pSMC/VP3, respectively;
5) amplifying DNA fragments containing VP0, VP1 or VP3 using pSMK/VP0, pSMA/VP1 and pSMC/VP3 as templates and GSTF/VP0GSTR, GSTF/VP1GSTR and GSTF/VP3GSTR as primers, respectively; digesting the DNA fragments and the vector pGEX4T-1 using restriction enzymes BamHI/XhoI, and inserting the digested DNA fragments into the vector pGEX4T-1, to yield recombinant expression vectors pGSTVP0, pGSTVP1 and pGSTVP3, respectively; wherein the GSTF has a sequence of SEQ ID NO: 19; the VP0GSTR has a sequence of SEQ ID NO: 20; the VP1GSTR has a sequence of SEQ ID NO: 21; the VP3GSTR has a sequence of SEQ ID NO: 22;

6) co-transforming the recombinant expression vectors pSMK/VP0, pSMA/VP1, pSMC/VP3, pGSTVP0, pGSTVP1 and pGSTVP3 in different combinations to an expression strain BL21 (DE3), each combination of the recombinant expression vector comprising the VP0, VP1 and VP3 genes; selecting for positive clones containing VP0, VP1 and VP3 genes by kanamycin, ampicillin and chloramphenicol combined with PCR amplification;

7) transferring the selected positive clones to an LB medium and culturing overnight at 180-220 rpm and 37° C.; inoculating a resulting bacterial solution on the LB medium at a ratio of 1:100 and continuing culturing at 180-220 rpm and 37° C. until the OD600 value of the bacterial solution reaches 0.6-1.2; inducing bacterial expression using IPTG at a concentration of 0.01-0.5 mM at 16-25° C. overnight; collecting cell pellets by centrifugation at 5000 rpm for 30 min, and storing at −20° C.;

8) resuspending the bacterial pellets with a buffer A in an ice bath; ultrasonicating the bacterial pellets and centrifuging at 12,000×g for 30 min; collecting a resulting supernatant and mixing with Ni-NTA His•Bind Resins at 4° C. for 30-60 min; removing heteroproteins with the buffer A and eluting target proteins with a buffer B; storing at −70° C.; wherein the buffer A contains 20 mM Tris-HCl, 500 mM NaCl, 5 mM Imidazol, pH=8.5; the buffer B contains 20 mM Tris-HCl, 500 mM NaCl, 300 mM Imidazol, pH=8.5; and 9) digesting the target proteins using small ubiquitination-modified proteases, splicing resulting products to yield virus-like particles of SVA.

The recombinant expression vectors pSMK/VP0, pGST/VP1 and pSMC/VP3 are co-transformed into the expression strain BL21 (DE3).

9) (above) can be implemented as follows: 20 μg of the target proteins, 200 μL of a digestion buffer, and 10 μL of the small ubiquitin-modified proteases are incubated at 37° C. for 30 min; and the digestion buffer contains 50 mM Tris-HCl, 150 mM NaCl, and 1 mM CaCl2, pH 8.0.

The disclosure also provides a method of preparing a vaccine comprising mixing the virus-like particles of the Senecavirus A with an adjuvant.

Also provided is a method of preparing a diagnostic reagent comprising employing the virus-like particle as an antigen.

The following advantages are realized: the expression level of the target proteins and the assembly efficiency of the virus-like particles are improved.

DETAILED DESCRIPTION

Figure 1:
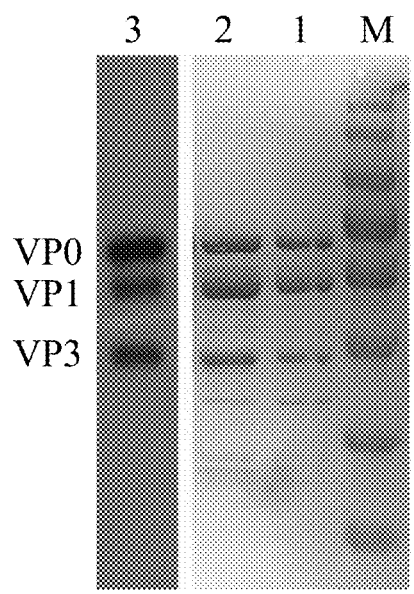
FIG. 1 shows SDS-PAGE and immunoblotting detection of SVA recombinant protein; M: quality standard of protein molecules; 1, 2: SDS-PAGE of purified SVA recombinant proteins; 3: immunoblotting of recombinant proteins.

To further illustrate, embodiments detailing a virus-like particle of Senecavirus A and a method for preparing the same are described below. It should be noted that the following embodiments are intended to describe and not to limit the disclosure.

Example 1 Preparation of Virus-Like Particles of SVA

1. Construction of Fusion Expression Vectors pSMA, pSMK and pSMC of Small Ubiquitin-Like Modified Proteins:

(1) amplifying the smt3 gene by employing the genomic DNA of *Saccharomyces cerevisiae* as a template and smt3F and smt3R as primers, where the sequence of smt3F and smt3R are as follows:

smt3F:
(SEQ ID NO: 4)
5' GCCATGGGTCATCACCATCATCATCACGGGTCGGACTCAGAAGTCAA TCAA 3' smt3R:
(SEQ ID NO: 5)
5' GGATCCGAGACCTTAAGGTCTCAACCTCCAATCTGTTCGCGGTG 3';

(2) Digesting the smt3 gene and a vector pET-28a using restriction enzymes Nco I and BamH I, inserting the digested smt3 gene into the digested pET-28a vector, to yield a vector pSMK;

Employing the pUC19 plasmid as a template, and using AmpRKpnI and AmpRNheI as primers to amplify a pSMK gene. Using PSMKKpnI and PSMKNheI as primers to amplify a DNA fragment from the pSMK, digesting the DNA fragment and the AmpR gene with restriction enzymes KpnI and NheI, and inserting the digested AmpR gene into the digested DNA fragment, to yield a vector pSMA. Employing the pACYC plasmid as a template, and using CmRKpnI and CmRNheI as primers to amplify a pSMK gene. Using PSMKKpnI and PSMKNheI as primers to amplify the DNA fragment from the pSMK, digesting the DNA fragment and the CmR gene with restriction enzymes KpnI and NheI, and inserting the digested CmR gene into the digested DNA fragment, to yield a vector pSMC. The sequence of AmpRKpnI is SEQ ID NO: 7, the sequence of AmpRNheI is SEQ ID NO: 8, the sequence of PSMKKpnI is SEQ ID NO: 9, the sequence of PSMKNheI is SEQ ID NO: 10, the sequence of CmRKpnI is SEQ ID NO: 11 and the sequence of CmRNheI is SEQ ID NO: 12. The sequences of these genes are as follows:

AmpRKpnI:
(SEQ ID NO: 7)
5' GGC GGT ACC AAT AAC CCT GAT AAA TGC 3'

AmpRNheI:
(SEQ ID NO: 8)
5' CCGC GCT AGC ATG AGA TTA TCA AAA AGG 3'

PSMKKpnI:
(SEQ ID NO: 9)
5' GTC GGT ACC GAA TTA ATT CAT GAG CGG 3'

PSMKNheI:
(SEQ ID NO: 10)
5' TCA GCT AGC GAC CAA AAT CCC TTA ACG 3'

CmRKpnI:
(SEQ ID NO: 11)

-continued

```
           5' AAT GGT ACC AAA AAA TTA CGC CCC GCCCT 3'

CmRNheI:
                                        (SEQ ID NO: 12)
           5' CTG GAC GCT AGC CAC CAT CAT ACACTA-3'
```

2. Construction of a Recombinant Expression Vector of SVA Structural Protein Gene Optimizing the codons and synthesizing the gene sequences encoding structural proteins VP0, VP1 and VP3 according to the SVA sequences (GenBank Number: NC_011349).

Using the synthetic gene as a template, the VP0, VP1 and VP3 gene fragments were amplified using the following primer pairs:

```
VP0F:
                                        (SEQ ID NO: 13)
           5' GGTCTCTAGGT GGCAACGTTCAAACCACC 3';

VP0R:
                                        (SEQ ID NO: 14)
           5' CGCGGATCCTCA CTGTTCCTCATCGGTACC 3';

VP1F:
                                        (SEQ ID NO: 15)
           5' GGTCTCTAGGT AGCACCGACAACGCGGAG 3';

VP1R:
                                        (SEQ ID NO: 16)
           5' CGCGGATCCTCA TTGCATCAGCATTTTCTG 3';

VP3F:
                                        (SEQ ID NO: 17)
           5' GGTCTCTAGGT GGTCCGATTCCGACCGCG 3';

VP3R:
                                        (SEQ ID NO: 18)
           5' CGCGGATCCTCAGTGAAAAACATAGCTCGG 3';
```

Using the polymerase chain reaction (PCR) method, the gene fragments encoding the structural proteins VP0, VP1 and VP3 were amplified by primers VP0F/VP0R, VP1F/VP1R and VP3F/VP3R, respectively. The gene sequence encoding structural protein VP0 was SEQ ID NO: 1, the gene sequence encoding structural protein VP1 was SEQ ID NO: 2, and the gene sequence encoding structural protein VP3 was SEQ ID NO: 3.

Digesting the amplified coding genes of the structural proteins VP0, VP1, and VP3 using the restriction enzymes BsmBI/BamH I, digesting the vector pSMK and pSMA using the restriction enzyme BsaI, inserting the digested coding genes of the structural proteins VP0, VP1, and VP3 into the digested pSMK or pSMA, to yield recombinant expression vectors pSMK/VP0, pSMK/VP1, and pSMA/VP3, respectively.

Using pSMK/VP0, pSMA/VP1 and pSMC/VP3 as templates, DNA fragments containing VP0, VP1 or VP3 were amplified with GSTF/VP0GSTR, GSTF/VP1GST and GSTF/VP3GSTR primer pairs, respectively. Digesting the DNA fragments and the vector pGEX4T-1 using restriction enzymes BamHI/XhoI, to yield the recombinant expression vector pGSTVP0, pGSTVP1 and pGSTVP3, respectively; where the gene sequences of the primers GSTF/VP0GSTR, GSTF/VP1GST and GSTF/VP3GSTR are as follows:

```
GSTF:
                                        (SEQ ID NO: 19)
           5' GGCAATGGATCCATGGGTCATCACCATCATCATCAC;

VP0GSTR:
                                        (SEQ ID NO: 20)
           5' GGTAATCTCGAGTTACTGTTCCTCATCGGTACCGG;

VP1GSTR:
                                        (SEQ ID NO: 21)
           5' GGCCGTCTCGAGTTATTGCATCAGCATTTTCTGC;

VP3GSTR:
                                        (SEQ ID NO: 22)
           5' GGCCTTCTCGAGTTAGTGAAAAACATAGCTCGGG.
```

3. Expression, Purification and Immunoblotting of SVA Recombinant Protein (1) Expression of Recombinant Protein The recombinant expression vectors pSMK/VP0, pSMA/VP1, pSMC/VP3, pGSTVP0, pGSTVP1 and pGSTVP3 were grouped in different combinations where each combination contains VP0, VP1 and VP3 genes, the combinations were co-transformed to the expression strain BL21 (DE3). For example, pSMK/VP0, pSMA/VP1, and pSMC/VP3 were grouped into a combination, pSMK/VP0, pSMA/VP1, and pGSTVP3 were grouped into a combination, or pSMK/VP0, pGSTVP1, and pSMC/VP3 were grouped into a combination and so on.

Selecting for positive clones containing VP0, VP1 and VP3 genes by kanamycin, ampicillin and chloramphenicol combined with PCR amplification. Transferring the selected positive clones to the LB medium and scale-up culturing them overnight at 180-220 rpm and 37° C. Inoculating the cultured bacterial solution on the LB medium at a ratio of 1:100 and culturing at 37° C. at 180-220 rpm until the OD600 value of the bacterial solution reached 0.6-1.2.

Inducing bacterial expression using IPTG at a concentration of 0.01-0.5 mM at 16-25° C. overnight. Finally, the cell pellets were collected by centrifugation at 5000 rpm for 30 min, and stored at −20° C.

(2) Purification of Expressed Proteins

Resuspending the bacterial pellets with a buffer A (20 mM Tris-HCl, 500 mM NaCl, 5 mM Imidazol, pH=8.5) in an ice bath. Ultrasonicating the bacterial pellets and centrifuging for 30 min at 12,000×g. Collecting the resulting supernatant and mixing with Ni-NTA His•Bind Resins at 4° C. for 30-60 min; removing heteroproteins with the buffer A and eluting the target proteins with a buffer B; storing at −70° C. The results of SDS-PAGE showed that the proteins with expected molecular sizes were obtained and the combination of different vectors has a significant effect on the expression and purification of the target proteins. The protein expressed by the expression plasmid transfected with pSMK/VP0, pGST/VP1 and pSMC/VP3 was the most ideal, and the ratio of the expression levels of VP0, VP1 and VP3 was closest to 1:1:1.

(3) Immunoblotting Experiment

Subjecting the eluted recombinant protein to 10% SDS-PAGE electrophoresis, and electrotransferring the recombinant protein to a polyvinylidene fluoride hybrid membrane (PVDF membrane) by wet transfer. Thereafter, the recombinant protein was blocked with a blocking solution (PBST, 5% skim milk powder, pH 7.0) at 37° C. for 1 h. SVA positive serum was diluted with PBST 1:200, rested at 37° C. for 1 hour, and washed. The rabbit anti-swine IgG labeled with horseradish peroxidase was diluted with PBST 1:3000, rested at 37° C. for 1 h, and washed with PBST; the luminescent substrate was added to a dark chamber for 3 min and exposed to Kozak film. After the development and fixation, the bands of the protein were observed and had the expected size, indicating that the obtained protein was a specific target protein capable of reacting with the SVA-positive serum (FIG. 1).

4. In-Vitro Assembly of SVA Virus-Like Particles

The fusion proteins were digested with small ubiquitin-like modifier proteases, and then spliced to form virus-like particles, following Invitrogn's reagent instructions. The procedure was as follows: 20 μg of the above purified fusion proteins, 200 μL of digestion buffer (50 mM Tris-HCl, 150 mM NaCl, pH 8.0, 1 mM $CaCl_2$), and 10 μL of small ubiquitin-like modifier protease (1 U/μL) were incubated at 37° C. for 30 min.

Figure 2:
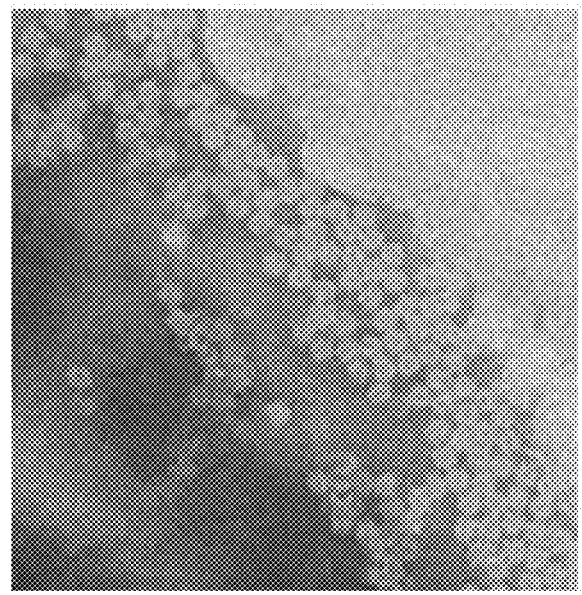
FIG. 2 is an image of SVAVLPs under transmission electron microscopy.

Observation by transmission electron microscopy: 10 μL of the liquid containing VLPs was added to a 200-mesh copper mesh, holding for 2-3 minutes at room temperature. The excess liquid on the copper mesh was removed with filter paper and then the VLPs were stained with 3% phosphotungstic acid, and observed under Hitachi, H-7100FA transmission electron microscopy. As shown in FIG. 2, the diameter of the assembled virus-like particles was between 20-30 nm, and its morphology and size were similar to those of natural virions.

5. Determination of Purification and Assembly Rate of Virus-Like Particles

Purifying virus-like particles by sucrose density gradient centrifugation: 1 mL of virus-containing particles were placed over a sucrose gradient of 20%-45% and centrifuged at 35,000 rpm and 4° C. for 3 h. The absorbances at OD280 nm of the sample were measured to calculate the assembly efficiency of the VLPs. The results showed that the assembly rate of the VLPs expressed by the expression plasmids transfected with pSMK/VP0, pGST/VP1 and pSMC/VP3 was the highest.

Example 2 Immunogenicity of SVA Virus-Like Particles

The antigen for immunization was emulsified with Freund's adjuvant. Fifteen guinea pigs of about 300 g were randomly divided into 3 groups, the first group was immunized with the VLPs (prepared in Example 1), the second group was immunized with unassembled protein, and the third group was injected with PBS as a control. Blood was collected on the 28th day after immunization and serum was separated to detect antibody titers and neutralizing antibodies in the antibody.

(1) ELISA Detection of Antibody Titer

The 96-well microtiter plate was coated with the SVA hyper-immune serum diluted with 100 μL of 0.05 M sodium carbonate buffer (pH 9.6) overnight at 4° C. After being washed 3 times with PBST, the microtiter plate was incubated with SVA virus solution at 37° C. for 1 h, then washed 3 times with PBST. The well plate was blocked with PBST (100 μL) containing 5% skim milk powder at 37° C. for 1 h. After being washed 3 times with PBST, the serum to be detected was diluted 1:100 with PBST containing 1% skim milk powder. 100 μL per well was added to the closed well plate and incubated at 37° C. for 1 h. After being washed 3 times with PBST, HRP-labeled rabbit anti-guinea pig IgG antibody (Sigma) was diluted 1:3000 with PBST containing 1% skim milk and added to a closed well plate at 100 μL per well, and incubated at 37° C. for 1 h. After being washed 3 times with PBST, 50 μL of a substrate solution (TMB, Sigma) was added to each well and incubated at 37° C. for 15 min. Then 50 μL of 2N $H_2SO_4$ was added to each well and the optical density (OD value) at 450 nm was detected.

Figure 3:
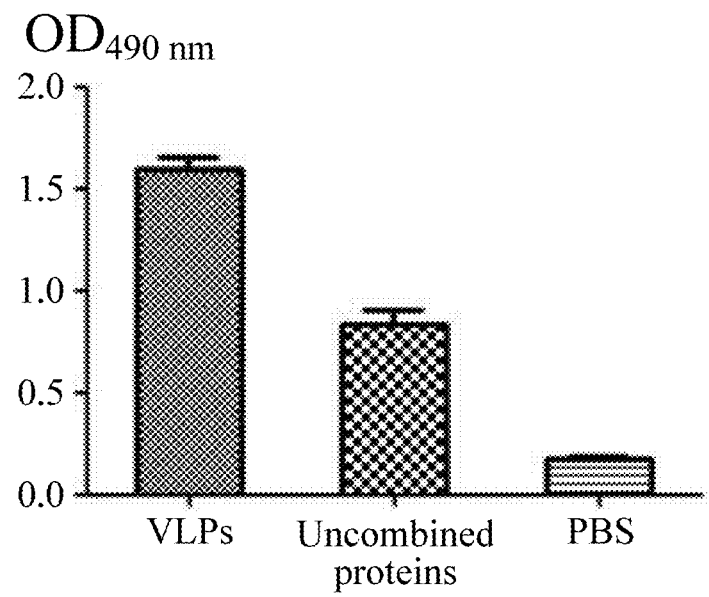
FIG. 3 shows the detection results of antibodies in serum of SVA VLPs immunized animals using ELISA.

The results showed that the antibody levels of the serum of the VLPs immunized group were significantly higher than those of the immunized group containing no VLPs and the PBS control group, and the difference was significant ($P<0.01$) (FIG. 3).

(2) Detection of Neutralizing Antibodies in Serum

The titer of neutralizing antibodies in the serum was measured by a microneutralization test. The physiologically diluted serum was inactivated at 56° C. for 30 min, and then diluted twice with DMEM nutrient solution on a 96-well microplate. Each dilution was provided with four wells, and 50 μL of virus solution (100 TCID50) was added to each well. After being incubated in a 37° C. incubator for 1 h, each well was added with 100 μL of cell suspension ($1 \times 10^5$ cells/mL), and cultured in a 5% $CO_2$ incubator at 37° C. for 48 h to 144 h. Positive and negative serum controls, virus regression tests, serum toxicity controls and normal cell controls were set up. According to the Spearman-Karber method, a serum dilution capable of protecting 50% of the cell well from cytopathic effect is calculated, which is the titer of the neutralizing antibodies in the serum.

Figure 4:
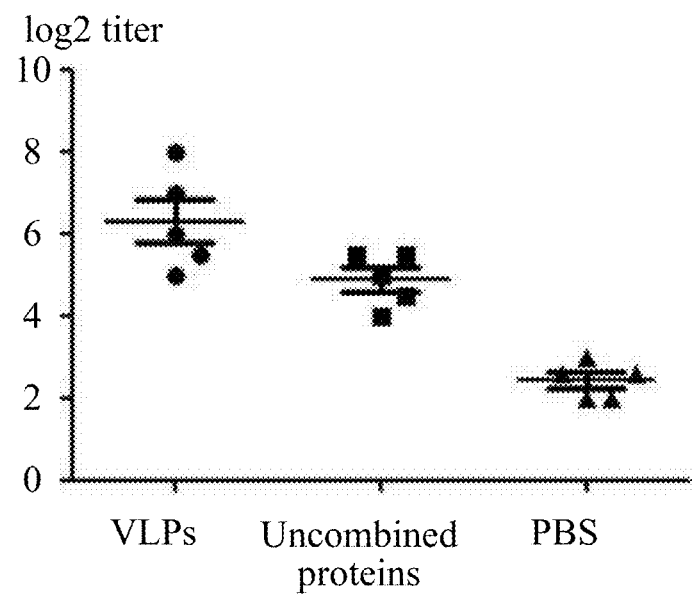
FIG. 4 shows the detection results of neutralizing antibodies in serum of SVA VLPs immunized animals.

The results showed that the titer of the neutralizing antibodies in the serum of the VLPs immunized group was 1:32-1:256, and the titer of the neutralizing antibodies in the serum of the group containing no immune proteins was 1:16-1:45, which testified the immune advantages of VLPs (FIG. 4).

It will be obvious to those skilled in the art that changes and modifications may be made, and therefore, the aim in the appended claims is to cover all such changes and modifications.

What is claimed is:

1. A virus-like particle, comprising:
a structural protein VP0 of Senecavirus A encoded by a gene sequence represented by SEQ ID NO: 1;
a structural protein VP1 of the Senecavirus A encoded by a gene sequence represented by SEQ ID NO: 2; and
a structural protein VP3 of the Senecavirus A encoded by a gene sequence represented by SEQ ID NO: 3.

2. A method, comprising:
1) amplifying a smt3 gene using genomic DNA of *Saccharomyces cerevisiae* as a template and smt3F and smt3R as primers, the smt3F having a sequence of SEQ ID NO: 4, the smt3R having a sequence of SEQ ID NO: 5, and the smt3 gene having a sequence of SEQ ID NO: 6;

2) digesting the smt3 gene and a vector pET-28a using restriction enzymes Nco I and BamH I, inserting the digested smt3 gene into the digested pET-28a vector, to yield a vector pSMK; amplifying an AmpR gene using a pUC19 plasmid as a template and AmpRKpnI and AmpRNheI as primers, amplifying a DNA fragment from the pSMK using PSMKKpnI and PSMKNheI as primers, digesting the DNA fragment and the AmpR gene with restriction enzymes KpnI and NheI, and inserting the digested AmpR gene into the digested DNA fragment, to yield a vector pSMA; amplifying a CmR gene using the pACYC plasmid as a template and CmRKpnI and CmRNheI as primers, amplifying a DNA fragment from the pSMK using PSMKKpnI and PSMKNheI as primers, digesting the DNA fragment and the CmR gene with restriction enzymes KpnI and NheI, and inserting the digested CmR gene into the digested DNA fragment, to yield a vector pSMC; wherein the AmpRKpnI has a sequence of SEQ ID NO: 7, the AmpRNheI has a sequence of SEQ ID NO: 8, the PSMKKpnI has a sequence of SEQ ID NO: 9, the PSMKNheI has a sequence of SEQ ID NO: 10, the CmRKpnI has a sequence of SEQ ID NO: 11, and the CmRNheI has a sequence of SEQ ID NO: 12:

3) synthesizing coding genes of the structural proteins VP0, VP1 and VP3; amplifying the coding genes of the structural proteins VP0, VP1, and VP3 using the synthesized coding genes of the structural proteins VP0, VP1, and VP3 as templates and VP0F/VP0R, VP1F/VP1R, and VP3F/VP3R as primers, respectively; wherein a coding gene of the structural protein VP0 is represented by SEQ ID NO: 1, a coding gene of the structural protein VP1 is represented by SEQ ID NO: 2, and a coding gene of the structural protein VP3 is represented by SEQ ID NO: 3; the VP0F has a sequence of SEQ ID NO: 13, the VP0R has a sequence of SEQ ID NO: 14, the VP1F has a sequence of SEQ ID NO: 15, the VP1R has a sequence of SEQ ID NO: 16, the VP3F has a sequence of SEQ ID NO: 17, the VP3R has a sequence of SEQ ID NO: 18;

4) digesting the amplified coding genes of the structural proteins VP0, VP1, and VP3 using the restriction enzymes BsmBI/BamH I, digesting the vector pSMK, pSMA or pSMC using the restriction enzyme BsaI, inserting the digested coding genes of the structural proteins VP0, VP1, and VP3 into the digested pSMK, pSMA or pSMC, to yield recombinant expression vectors pSMK/VP0, pSMA/VP1, and pSMC/VP3, respectively;

5) amplifying DNA fragments containing VP0, VP1 or VP3 using pSMK/VP0, pSMA/VP1 and pSMC/VP3 as templates and GSTF/VP0GSTR, GSTF/VP1GSTR and GSTF/VP3GSTR as primers, respectively; digesting the DNA fragments and the vector pGEX4T-1 using restriction enzymes BamHI/XhoI, and inserting the digested DNA fragments into the vector pGEX4T-1, to yield recombinant expression vectors pGSTVP0, pGSTVP1 and pGSTVP3, respectively; wherein the GSTF has a sequence of SEQ ID NO: 19; the VP0GSTR has a sequence of SEQ ID NO: 20; the VP1GSTR has a sequence of SEQ ID NO: 21; the VP3GSTR has a sequence of SEQ ID NO: 22;

6) co-transforming the recombinant expression vectors pSMK/VP0, pSMA/VP1, pSMC/VP3, pGSTVP0, pGSTVP1 and pGSTVP3 in different combinations to an expression strain BL21 (DE3), each combination of the recombinant expression vector comprising the VP0, VP1 and VP3 genes; selecting for positive clones containing VP0, VP1 and VP3 genes by kanamycin, ampicillin and chloramphenicol combined with PCR amplification;

7) transferring the selected positive clones to an LB medium and culturing overnight at 180-220 rpm and 37° C.; inoculating a resulting bacterial solution on the LB medium at a ratio of 1:100 and continuing culturing at 180-220 rpm and 37° C. until the OD600 value of the bacterial solution reaches 0.6-1.2; inducing bacterial expression using IPTG at a concentration of 0.01-0.5 mM at 16-25° C. overnight; collecting cell pellets by centrifugation at 5000 rpm for 30 min, and storing at −20° C.;

8) resuspending the bacterial pellets with a buffer A in an ice bath; ultrasonicating the bacterial pellets and centrifuging at 12,000×g for 30 min; collecting a resulting supernatant and mixing with Ni-NTA His•Bind Resins at 4° C. for 30-60 min; removing heteroproteins with the buffer A and eluting target proteins with a buffer B; storing at −70° C.; wherein the buffer A contains 20 mM Tris-HCl, 500 mM NaCl, 5 mM Imidazol, pH=8.5; the buffer B contains 20 mM Tris-HCl, 500 mM NaCl, 300 mM Imidazol, pH=8.5; and 9) digesting the target proteins using small ubiquitination-modified proteases, splicing resulting products to yield virus-like particles of SVA.

3. The method of claim 2, wherein in 6), the recombinant expression vectors pSMK/VP0, pGST/VP1 and pSMC/VP3 are co-transformed into the expression strain BL21 (DE3).

4. The method of claim 2, wherein 9) is implemented as follows: 20 μg of the target proteins, 200 μL of a digestion buffer, and 10 μL of the small ubiquitin-modified proteases are incubated at 37° C. for 30 min; and the digestion buffer contains 50 mM Tris-HCl, 150 mM NaCl, and 1 mM CaCl2, and has a pH of 8.0.

5. A method comprising mixing the virus-like particle of claim 1 with an adjuvant to yield a vaccine.

6. A method comprising using the virus-like particle of claim 1 as an antigen.

* * * * *